United States Patent
Nierich (10) Patent No.: US 8,936,554 B2
(45) Date of Patent: Jan. 20, 2015

(54) METHOD AND SYSTEM FOR ULTRASONIC IMAGING OF AN ORGAN IN A PATIENT'S BODY THROUGH A PART OF THE PATIENT'S RESPIRATORY TRACT

(75) Inventor: Arno Nierich, CJ Hattem (NL)

(73) Assignee: Stroke2Prevent B.V., Hattem (NL)

( * ) Notice: Subject to any disclaimer, the term of this patent is extended or adjusted under 35 U.S.C. 154(b) by 1516 days.

(21) Appl. No.: 12/051,222

(22) Filed: Mar. 19, 2008

(65) Prior Publication Data

US 2008/0234584 A1 Sep. 25, 2008

Related U.S. Application Data

(63) Continuation-in-part of application No. 11/454,470, filed on Jun. 16, 2006, now Pat. No. 7,780,599, which is a continuation-in-part of application No. 10/221,250, filed as application No. PCT/EP00/02212 on Mar. 10, 2000, now abandoned.

(30) Foreign Application Priority Data

Mar. 10, 1999 (EP) .................................... 99200703

(51) Int. Cl.
*A61B 8/14* (2006.01)
*A61B 5/03* (2006.01)
*A61B 5/00* (2006.01)
*A61B 8/12* (2006.01)

(52) U.S. Cl.
CPC ............... *A61B 5/037* (2013.01); *A61B 5/6853* (2013.01); *A61B 8/12* (2013.01)
USPC ............................ 600/462; 600/459; 600/466

(58) Field of Classification Search
USPC ......................................................... 600/455
See application file for complete search history.

(56) References Cited

U.S. PATENT DOCUMENTS

| | | | | |
|---|---|---|---|---|
| 2,541,402 A | * | 2/1951 | Caine | 128/200.26 |
| 3,766,927 A | | 10/1973 | Jackson | |
| 3,779,234 A | | 12/1973 | Eggleton et al. | |
| 3,800,788 A | | 4/1974 | White | |
| 3,810,474 A | | 5/1974 | Cross | |
| 3,996,939 A | * | 12/1976 | Sheridan et al. | 128/207.14 |
| 4,244,362 A | * | 1/1981 | Anderson | 128/200.26 |

(Continued)

FOREIGN PATENT DOCUMENTS

JP 06285068 11/1994
WO 9104708 4/1991

*Primary Examiner* — Unsu Jung
*Assistant Examiner* — Michael Kellogg
(74) *Attorney, Agent, or Firm* — The Webb Law Firm (57) ABSTRACT

The invention relates to a method for ultrasonic imaging of an organ in a patient's body through a part of the patient's respiratory tract, including: arranging an ultrasonic imaging device in or on the patient's body; introducing a flexible catheter carrying at least one inflatable member into the respiratory tract; positioning the inflatable member at a predetermined location in the respiratory tract; filling the inflatable member with an ultrasonic transmission fluid through the flexible catheter; and transmitting ultrasonic waves from the imaging device through the transmission fluid in the inflatable member to the organ to be imaged. The inflatable member is positioned in the respiratory tract by manipulating guide means that are attached to or integrated with the flexible catheter. The invention further relates to an ultrasonic imaging system for carrying out this method and to an assembly means for use in such an ultrasonic imaging system.

8 Claims, 4 Drawing Sheets

(56) References Cited

U.S. PATENT DOCUMENTS

| | | | |
|---|---|---|---|
| 4,349,033 A | 9/1982 | Eden | |
| 4,391,282 A | 7/1983 | Ando et al. | |
| 4,466,443 A | 8/1984 | Utsugi | |
| 4,737,152 A * | 4/1988 | Alchas | 604/256 |
| 4,906,244 A | 3/1990 | Pinchuk et al. | |
| 4,947,827 A * | 8/1990 | Opie et al. | 600/108 |
| 4,979,505 A | 12/1990 | Cox | |
| 5,105,819 A | 4/1992 | Wollschlager et al. | |
| 5,190,046 A | 3/1993 | Shturman | |
| 5,331,947 A * | 7/1994 | Shturman | 600/115 |
| 5,409,483 A * | 4/1995 | Campbell et al. | 606/15 |
| 5,421,338 A * | 6/1995 | Crowley et al. | 600/463 |
| 5,788,665 A * | 8/1998 | Sekins | 604/19 |
| 5,980,462 A * | 11/1999 | Maruta | 600/462 |
| 6,488,673 B1 * | 12/2002 | Laufer et al. | 604/516 |
| 6,575,993 B1 * | 6/2003 | Yock | 606/194 |
| 7,774,933 B2 * | 8/2010 | Wilson et al. | 29/854 |
| 7,972,350 B2 * | 7/2011 | McHale et al. | 606/194 |
| 2003/0195510 A1 * | 10/2003 | Schaer | 606/41 |

\* cited by examiner

METHOD AND SYSTEM FOR ULTRASONIC IMAGING OF AN ORGAN IN A PATIENT'S BODY THROUGH A PART OF THE PATIENT'S RESPIRATORY TRACT

CROSS REFERENCE TO RELATED APPLICATIONS

This application is a continuation-in-part and claims the benefit of priority to U.S. patent application Ser. No. 11/454,470, filed Jun. 16, 2006, which is a continuation-in-part application of U.S. application Ser. No. 10/221,250, filed Sep. 10, 2002, which claims the benefit of priority to PCT Application No. PCT/EP00/02212, filed Mar. 10, 2000 and European Application No. 99200703.9, filed Mar. 10, 1999, which are incorporated herein by reference in their entirety.

BACKGROUND OF THE INVENTION

1. Field of the Invention

The invention relates to a method for ultrasonic imaging of an organ in a patient's body through a part of the patient's respiratory tract.

2. Description of Related Art

Such a method is known from WO 00/53098. This prior art document relates to an ultrasonic imaging method that is known as transesophageal echocardiography (TEE). TEE has become a widely used imaging technique for evaluating cardiac structure, function, and valvular anatomy. TEE has also provided a new perspective on the thoracic aorta, and there is growing evidence that the technique contributes valuable and sometimes unique information about aortic structure and pathology.

TEE involves introducing an echo probe into the patient's esophagus and transmitting ultrasound waves across the thorax in the direction of the heart and aorta. However, visualization of the ascending aorta by internal TEE is limited by an air structure, i.e. the trachea and main left and right bronchi. This is due to an important physical limitation of ultrasound: absorption of ultrasound waves. This absorption is dependent of the medium and expressed in terms of the "half power distance": the distance in which half of the ultrasound energy will be absorbed. For water this is 360 cm, bone 0.2 cm and for air 0.06 cm. This means that in practice ultrasound waves will not travel through bone or air.

Unfortunately, by the anatomical location of the aorta ascendens and the upper part of the main vascular side branches, it is difficult to view this area by TEE because the view is obstructed by the trachea. The trachea is located between the esophagus and the vascular tree, so all echoes are reflected by the trachea, which is filled with air.

In order to solve this problem, WO 00/53098 proposes the use of a balloon that may be arranged in the trachea or in one of the bronchi and that may be filled with an ultrasonic transmission fluid, e.g. water or a saline solution in minor concentrations. Obviously, this can only be done during operative surgery, when the patient is mechanically ventilated or on cardiopulmonary bypass, since in order to be effective the balloon has to completely fill and block the trachea or bronchus.

A problem which arises when trying to introduce the balloon in the left bronchus, which is the position of choice when visualizing the aorta ascendens, is that the flexible catheter carrying the balloon is hard to manipulate. Therefore, positioning the distal end of this flexible catheter in front of the left bronchus, so that the balloon may be lowered into that bronchus, is often a matter of trial and error. Since this positioning has to be performed during operative surgery, when timing is often critical, there is a clear need for an improved imaging method.

SUMMARY OF THE INVENTION

In accordance with the invention, provided is a method for ultrasonic imaging. An inflatable member is positioned in the respiratory tract by manipulating guide means that are attached to or integrated with the flexible catheter. By providing the flexible catheter with dedicated guide means, its movement through the respiratory tract may be precisely controlled.

In a preferred variant of the method, the guide means are passive and comprise at least one stylet. Stylets are widely available and the skilled person is familiar with their operation.

The stylet may have a distal end which extends beyond the inflatable member and a proximal end which protrudes outside the patient's body, so that the inflatable member may be positioned in the respiratory tract by manipulating this proximal end.

In order to prevent the stylet from obstructing part of the area to be imaged from view, the stylet is preferably at least partially retracted before the ultrasonic waves are transmitted from the imaging device.

In that case, it is advantageous when the proximal end of the stylet protrudes from the catheter through a valve member, so that the stylet may be retracted after the inflatable member has been filled with the transmission fluid, without the risk of fluid leaking from the system.

In a preferred variant of the method of the invention the stylet is made from a resilient material and is preformed to conform substantially to the intended path of the catheter through the respiratory tract for positioning the inflatable member before being attached to or integrated with the flexible catheter. In this way the flexible catheter assumes the shape of the stylet. If the stylet and catheter are partially guided through an endotracheal ventilation tube they will return to their slightly curved preformed shape when leaving that tube, after which the distal end of the catheter carrying the inflatable member may be easily directed to the left bronchus by manipulating the stylet.

In another variant of the method, on the other hand, the stylet is made from a deformable material and conforms substantially to the respiratory tract when the flexible catheter and inflatable member are introduced therein. In this way, the stylet and catheter will conform to the endotracheal tube through which they pass. After leaving the tube the material of the stylet will maintain the curved shape into which it was forced by the tube, so that the distal end of the catheter can again easily be guided to its predetermined position.

In yet another variant, the stylet is made from a resilient material and is substantially straight, so that after passing curved parts of the respiratory tract during introduction of the flexible catheter and inflatable member therein at least the distal end of the stylet and the catheter will run straight. In this way the distal end will be eccentric with respect to the endotracheal tube, which is somewhat curved. This again facilitates positioning of the distal end of the catheter and ultimately of the inflatable member.

It is also conceivable that a relatively short stylet is used, which is arranged between the inflatable member and a distal end of the catheter, in which case the inflatable member may be positioned in the respiratory tract by manipulating a proximal end of the flexible catheter. By using only such a short stylet, which will not obstruct the view through the inflatable member, there is no need to retract the stylet before imaging. Consequently, there is no risk of any fluid leaking from the system, so that the valve member may be dispensed with. This short stylet may also be either straight or preformed in a suitable shape.

In yet another variant of the method of the invention the guide means are active and comprise at least one pull wire having a distal end that is eccentrically connected to the flexible catheter and a proximal end connected to a pulling member arranged outside the patient's body, and the inflatable member is positioned in the respiratory tract by manipulating the pulling member. The use of such a pull wire allows a very precise positioning of the distal end of the catheter carrying the inflatable member.

Although the wire could in principle run along the outside of the catheter, it is preferable to arrange the wire in the catheter, in which case its proximal end may protrude from the catheter through a valve member. In this way the system may be filled with fluid and vented with the wire in place, without the risk of leaking.

The guide means may include a plurality of pull wires that are spaced at least in peripheral direction of the catheter, each said pull wire being connected to a respective pulling member, so that the inflatable member may be positioned in the respiratory tract by selectively manipulating the various pulling members. In this way the catheter may be controlled in different directions.

The invention further relates to a system for ultrasonic imaging of an organ in a patient's body through a part of the patient's respiratory tract with which the above method may be performed. A prior art imaging system of this type, which is also disclosed in WO 00/53098, includes:

an ultrasonic imaging device arranged in or on the patient's body, a flexible catheter carrying at least one inflatable member to be arranged in the respiratory tract, means for positioning the inflatable member at a predetermined location in the respiratory tract, and means for filling the inflatable member with an ultrasonic transmission fluid through the flexible catheter.

The ultrasonic imaging system of the present invention is distinguished from this prior art system in that the positioning means comprise guide means that are attached to or integrated with the flexible catheter. These guide means allow the inflatable member carried by catheter to be swiftly and easily guided to its predetermined position.

In a first preferred embodiment of the ultrasonic imaging system of the invention the guide means may be passive and comprise at least one stylet. As stated above, the stylet may advantageously be arranged in the catheter and may have a distal end which extends beyond the inflatable member and a proximal end which protrudes from the catheter.

In a further development of this embodiment, the catheter may have a main lumen for filling the inflatable member with the ultrasonic transmission fluid, the stylet being arranged in this main lumen. In this way no structural modification of the catheter is required.

Alternatively, the catheter may have a main lumen for filling the inflatable member with the ultrasonic transmission fluid and an additional lumen for accommodating the stylet. This additional lumen avoids any interference between the introduction and withdrawal of the stylet on one hand and filling or emptying the catheter on the other.

In these embodiments the stylet may be slidably arranged in the catheter and its proximal end may protrude from the catheter through a valve member to prevent leakage, as explained above.

In yet another embodiment of the ultrasonic imaging system the catheter may have a main lumen for filling the inflatable member with the ultrasonic transmission fluid and the stylet may be fixedly arranged in a peripheral wall surrounding the main lumen. In this case a very thin stylet is used, which does not adversely affect the ultrasonic imaging in any substantial way.

Rather than a long stylet extending over the entire length of the catheter, the ultrasonic imaging system may include a short stylet, which may be arranged between the inflatable member and a distal end of the catheter. Since this stylet does not extend across the inflatable member, it will not interfere with the imaging. This short stylet may also be arranged either in the main lumen, in an additional lumen or in the peripheral wall of the catheter.

In this embodiment the distal end of the catheter preferably includes a tip that is shaped to facilitate positioning in the patient's left main bronchus and the stylet is adhesively fixed to the catheter tip. In this way the stylet and tip cooperate to allow the inflatable member to be optimally positioned.

In yet another embodiment of the ultrasonic imaging system of the invention the guide means are active and comprise at least one wire having a distal end that is eccentrically connected to the flexible catheter and a proximal end connected to a pulling member arranged outside the patient's body. Such a wire provides excellent guidance of the catheter with minimum obstruction of the image.

In order to provide optimum control the distal end of the pull wire is preferably connected to the flexible catheter near a distal end thereof.

When the catheter has a main lumen for filling the inflatable member with the ultrasonic transmission fluid and the pull wire is arranged in the main lumen the system may be used with a minimum of structural modifications to the catheter.

In an alternative embodiment of the ultrasonic imaging system the catheter, which has a main lumen for filling the inflatable member with the ultrasonic transmission fluid, may have an additional lumen for accommodating the pull wire. In this way interference between the pull wire and the transmission fluid is minimized.

In order to prevent fluid leakage, the proximal end of the or each pull wire preferably protrudes from the catheter through a valve member.

In yet another embodiment of the system the catheter has a main lumen for filling the inflatable member with the ultrasonic transmission fluid and the pull wire is fixedly arranged in a peripheral wall surrounding the main lumen, so that no valve member is required.

When the ultrasonic imaging system comprises a plurality of pull wires having their distal ends eccentrically connected to the flexible catheter, the pull wires being spaced at least in peripheral direction of the catheter, the catheter may be controlled in different directions.

Finally, the invention relates to an assembly of a flexible catheter carrying at least one inflatable member positioning means for use in the ultrasonic imaging system as described above.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE PREFERRED EMBODIMENTS

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

It is to be understood that the invention may assume various alternative variations and step sequences, except where expressly specified to the contrary. It is also to be understood that the specific devices and processes illustrated in the attached drawings, and described in the following specification, are simply exemplary embodiments of the invention.

A method for ultrasonic imaging of an organ in a patient's body 1, in particular the heart or the aorta 2, through a part of the patient's respiratory tract 3, comprises the following steps.

Figure 1:
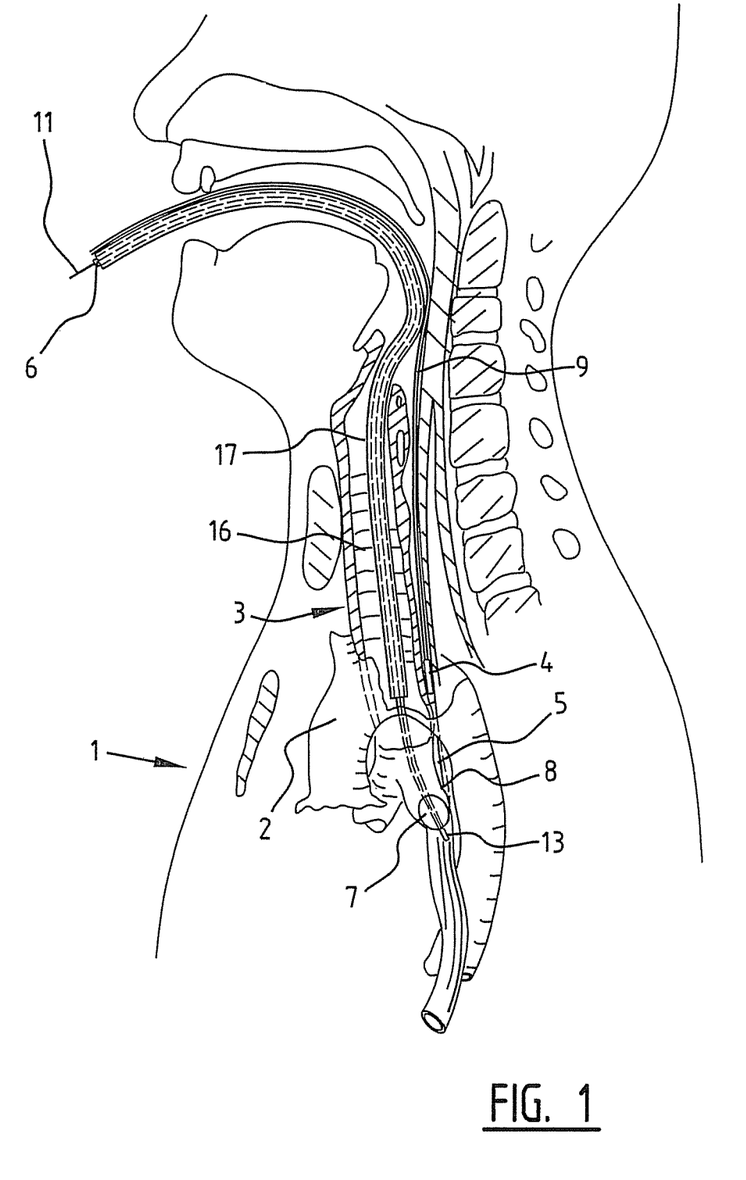
FIG. 1 is a partial sectional view of a patient's upper body showing the ultrasonic imaging system of the invention during visualization of an organ.

First an ultrasonic imaging device 4, for instance an echo probe, is arranged in or on the patient's body 1. In the shown embodiment, the echo probe 4, which is carried on a flexible catheter 9, is introduced into the patient's esophagus 5 (FIG. 1). Then another flexible catheter 6 carrying an inflatable member 7 is introduced into the respiratory tract 3. The inflatable member 7 is positioned at a predetermined location in the respiratory tract 3. When the organ to be imaged is the ascending aorta 2, the predetermined position will be in the top part of the left bronchus 8.

In actual practice, the flexible catheter 6 carrying the inflatable member 7 will be guided through the patient's trachea 16 by first introducing an endotracheal tube 17 into the trachea 16. This tube 17 is somewhat stiffer than the catheter 6 and therefore easier to control. The catheter 6 is then inserted in the endotracheal tube 17. After leaving the endotracheal tube 17 the distal end 13 of the catheter 6 and the inflatable member 7 are guided into the left bronchus 8.

Figure 2:
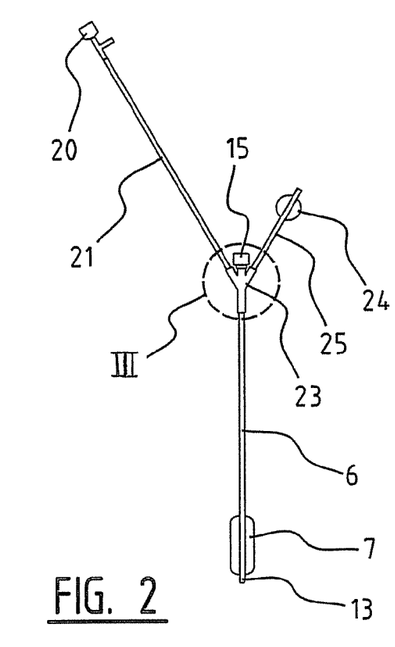
FIG. 2 is a schematic view of a first embodiment of the ultrasonic imaging system of the invention, including a full length stylet, showing the inflatable member filled with transmission fluid.
Figure 3:
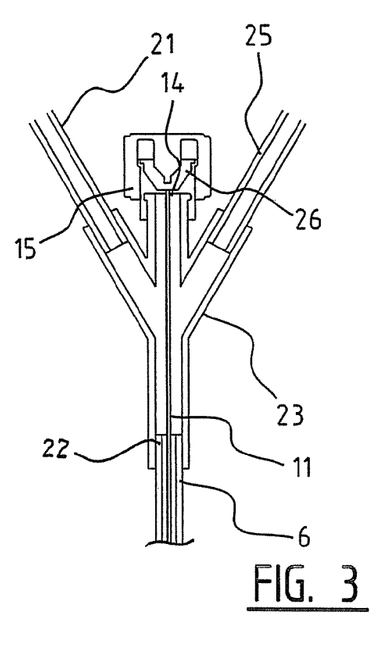
FIG. 3 is a detailed, enlarged scale view of the encircled area III in FIG. 2.

After the inflatable member 7 has been positioned, it is filled with an ultrasonic transmission fluid F through the flexible catheter 6. The fluid F is injected into the catheter 6 by means of a syringe (not shown), which is connected to a fill connector 20 at the end of a fill line 21 (FIG. 2). This fill line 21 in turn is connected to a proximal end 22 of the catheter 6 through a trident connector 23 (FIG. 3). The degree of filling of the inflatable member 7 may be visually determined by monitoring a pilot balloon 24, which is arranged at the end of a pilot line 25. This pilot line 25 is also connected to the catheter 6 through the trident connector 23.

When the degree of inflation of the pilot balloon 24 indicates that the inflatable member 7 has been filled to such an extent that it completely covers the entire cross-sectional area of the left bronchus 8, so that no air is present between the echo probe 4 and the organ 2 to be imaged, the echo probe 4 is activated. Ultrasonic waves are then transmitted from the echo probe 4 through the transmission fluid F in the inflatable member 7 to the ascending aorta 2. Reflections from the aorta 2 are received at the echo probe 4 and transmitted through a line running through the catheter 9 to a processing and display apparatus, which does not form part of the present invention and is not shown here.

Due to the presence of the inflatable member 7 that is filled with the transmission fluid F, e.g. water or a saline solution in minor concentrations, the ultrasonic waves can travel pass the respiratory tract 3 with virtually no absorption. Consequently, very good ultrasound images of the aorta 2 may be obtained. Obviously, this can only be done during operative surgery, when the patient is mechanically ventilated or on cardiopulmonary bypass, since in order to be effective the inflatable member 7 has to completely fill and block the left bronchus 8.

In order to properly visualize the aorta it is important that the inflatable member 7 be positioned in precisely the right location. In accordance with the present invention the inflatable member 7 is positioned in the respiratory tract by manipulating guide means 10 that are attached to or integrated with the flexible catheter 6.

In a first embodiment these guide means 10 are passive and include a stylet 11 that extends over the entire length of the flexible catheter 6. A distal end 12 of the stylet 11 extends beyond the inflatable member 7 to a distal end 13 of the catheter 6. A proximal end 14 of the stylet 11 protrudes from the proximal end 22 of the catheter 6 outside the patient's body 1 and extends into the center prong of the trident connector 23. This center prong is closed by a cap 15 carrying a valve member 26, the function of which will be described below. This arrangement allows the inflatable member 7 to be swiftly and accurately positioned in the respiratory tract 3, since the presence of the stylet 11 adds stiffness to the flexible catheter 6, thus improving directional control and predictability of the movement.

Figure 7A:
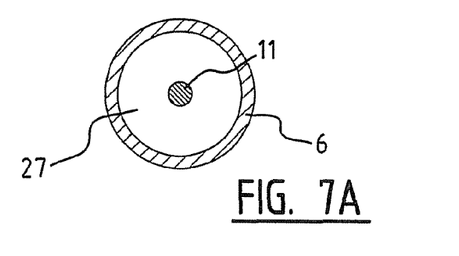
FIGS. 7A to 7C are cross-sectional views of the catheter, showing the various possibilities for accommodating the full length stylet.
Figure 7B:
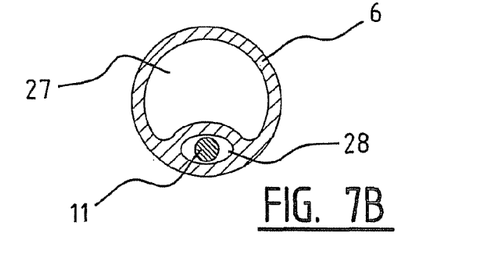

There are various possibilities for accommodating the full length stylet 11 in the catheter 6. In a first variant, which is structurally simple, the catheter 6 has a main lumen 27 for filling the inflatable member 7 with the ultrasonic transmission fluid F and the stylet 11 is arranged in the main lumen 27 (FIG. 7A). Alternatively, the catheter 6 may have a main lumen 27 for the ultrasonic transmission fluid F and an additional lumen 28 for accommodating the stylet 11 (FIG. 7B). In this way the stylet 11 does not interfere with the fluid supply function of the catheter 6.

In order to prevent the full length stylet 11 from obstructing part of the area to be imaged from view, it has to be at least partially retracted before the ultrasonic waves are transmitted from the imaging device 4. To that end the stylet 11 may be slidably arranged in either the main lumen 27 or the additional lumen 28. Although for proper imaging it would be sufficient to withdraw the stylet 11 only so far that its distal end 12 is on the proximal side of the inflatable member 7, in actual practice the stylet 11 will be completely withdrawn from the catheter 6, since it has served its purpose when the inflatable member 7 has been properly positioned. To allow the stylet 11 to be retracted after the inflatable member 7 has been filled with the transmission fluid F, without the risk of fluid F leaking from the system, the proximal end 14 of the stylet 11 protrudes from the catheter 6 through a valve member 26. In the illustrated embodiment this valve member 26 is a one-way valve that is arranged in the center prong of the trident connector 23.

Figure 7C:
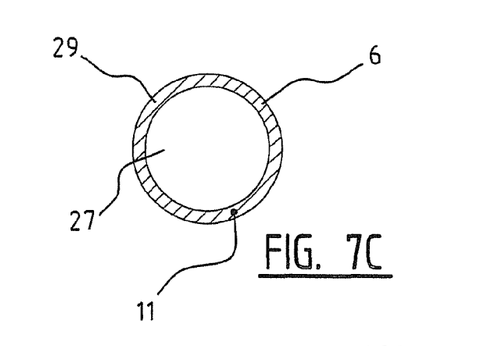

Alternatively, the stylet 11 may be fixedly arranged in a peripheral wall 29 surrounding the main lumen 27 of the catheter 6 (FIG. 7C). In this case a very thin stylet 11A is used, which does not adversely affect the ultrasonic imaging in any substantial way, and which therefore does not have to be retracted. This thin stylet 11A may be fixedly arranged in the catheter wall 29.

There are various possibilities for the stylet 11 and the catheter 6 carrying the inflatable member 7 to be guided to the predetermined position in e.g. the left bronchus 8.

Figure 4:
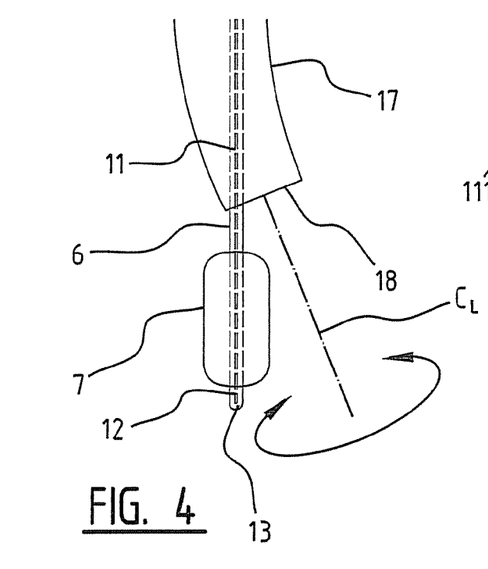
FIG. 4 is a schematic view on an exaggerated scale of the distal end of the flexible catheter according to a first embodiment of the invention.

In the illustrated embodiment the stylet 11 is made from a resilient material and is substantially straight. Consequently, the stylet 11 will always try to assume its original straight shape. When the flexible catheter 6 and the stylet 11 are guided through the endotracheal tube 17, which itself follows the curvature of the trachea 16, they will have to follow the curvature of the tube 17 as well. However, after leaving the distal end 18 of the endotracheal tube 17 the stylet 11 will return to its straight shape due to its resiliency. The part of the stylet 11 and the catheter 6 protruding from the distal end 18 of the tube 17 will therefore enclose an angle with an imaginary extension of the centerline $C_L$ of the tube 17. Consequently, rotating the proximal end 14 of the stylet 11 will lead to the distal end 12 describing a circular motion, which facilitates positioning of the distal end 13 of the catheter 6 at the entrance of the left bronchus 8 (FIG. 4).

Figure 5:
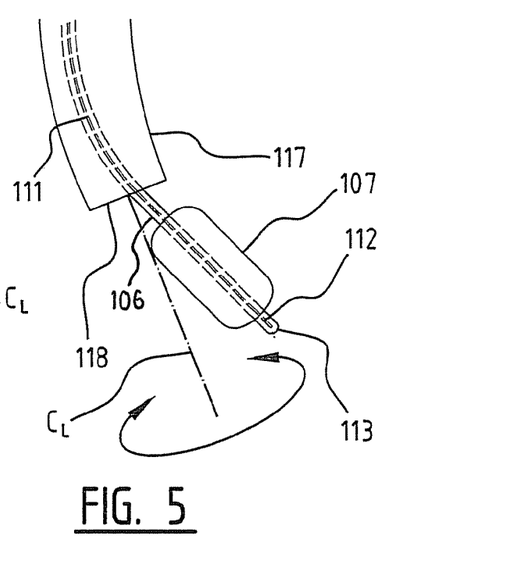
FIG. 5 is a schematic view on an exaggerated scale of the distal end of the flexible catheter according to a second embodiment of the invention.

In an alternative embodiment the stylet 111 is made from a resilient material and is preformed to conform substantially to the intended path of the catheter 106 through the respiratory tract 3. Preforming the stylet 111 may advantageously be done before it is attached to or integrated with the flexible catheter 106. In this way the catheter 106 assumes the shape of the stylet 111. When the flexible catheter 106 and the stylet 111 are guided through the endotracheal tube 117, which has less curvature than the stylet 111, they will be straightened somewhat. However, after leaving the distal end 118 of the endotracheal tube 117 the stylet 111 will return to its curved shape due to its resiliency, again extending under an angle with respect to the extension of the centerline $C_L$ of the tube 117. Therefore, also in this embodiment rotating the proximal end 114 of the stylet 111 will result in a circular motion of its distal end 112, thus allowing the distal end 113 of the catheter 106 to be positioned at the entrance of the left bronchus 8 (FIG. 5).

Figure 6:
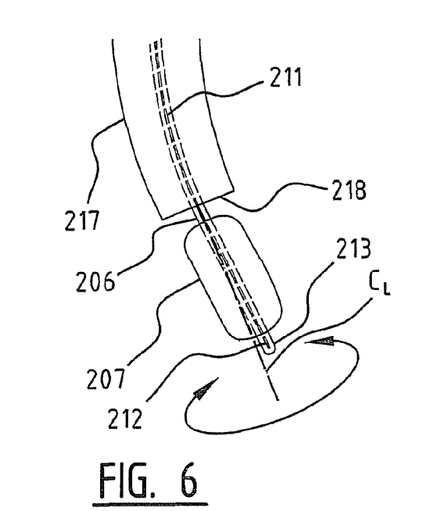
FIG. 6 is a schematic view on an exaggerated scale of the distal end of the flexible catheter according to a third embodiment of the invention.

In a third embodiment the stylet 211 is made from a deformable material. In this way, the stylet 211 will conform to the respiratory tract 3, or to the endotracheal tube 217, when the flexible catheter 206 including this stylet 211 passes through the trachea 16. After leaving the tube 217 the material of the stylet 211 will maintain the curved shape into which it was forced. Consequently, the distal end 213 of the catheter 206 will form a continuation of the curvature of the tube 217, so that it can again easily be guided to its predetermined position at the entrance of the left bronchus 8 (FIG. 6) by manipulating the proximal end of the stylet 211.

In yet another embodiment, the ultrasonic imaging system may include a short stylet 311, which may be arranged between the inflatable member 307 and the distal end 313 of the catheter 306 (FIG. 8), rather than a full length stylet. Since this short stylet 311 does not extend across the inflatable member 307, it will not interfere with the imaging and there is no need to retract it. The distal end 313 of the catheter 306 includes a tip 330 that is shaped to facilitate positioning in the patient's left main bronchus 8 and the stylet 311 is adhesively fixed to the catheter tip 330. In this way the stylet 311 and tip 330 cooperate to allow the inflatable member 307 to be optimally positioned.

Figure 8:
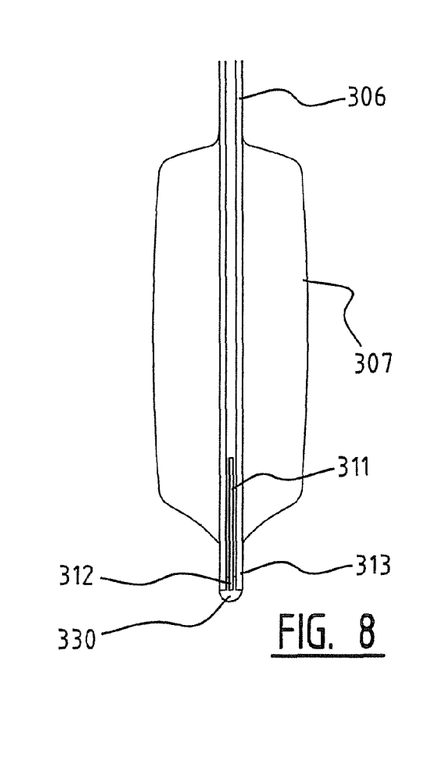
FIG. 8 is a detailed, enlarged scale view of the distal end of the catheter in a fourth embodiment of the invention, including a short stylet.

Since the stylet 311 does not extend beyond the distal end of the inflatable member 307, this embodiment will not have any part extending outside the patient's body 1. Positioning of the catheter 306 and the inflatable member 307 is done by manipulating the proximal end of the catheter 306. And since this stylet 311 does not have to be retracted from the catheter 306, there is no need for a special valve means.

Figure 9:
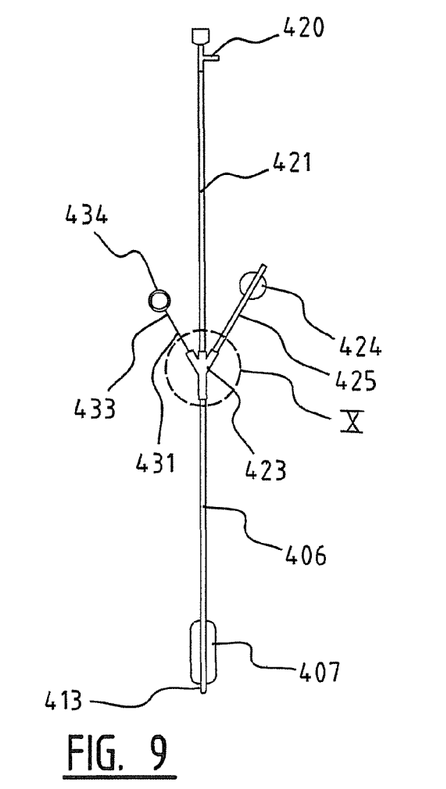
FIG. 9 is a schematic view of a fifth embodiment of the ultrasonic imaging system of the invention, including a pull wire.

In another main embodiment of the ultrasonic imaging system of the invention the guide means 410 comprise a wire 431 rather than a stylet. A distal end 432 of the wire 431 is eccentrically connected to the flexible catheter 406 and a proximal end 433 of the wire 431 is connected to a pulling member 434 arranged outside the patient's body 1 (FIG. 9). The wire 431, which is very thin, provides excellent guidance of the catheter 406 with minimum obstruction of the image. The inflatable member 407 is positioned in the respiratory tract 3 by manipulating the pulling member 434. By pulling on the wire 431, its effective length within the catheter 406 will decrease. Since the wire 431 is eccentrically attached to the catheter 406, shortening of the wire 431 will lead to the catheter 406 assuming a curved shape, at least in the vicinity of the point where the wire 431 is attached. In the illustrated embodiment this attachment point is located near the distal end 413 of the catheter 406. This location allows optimum control of the catheter 406.

Figure 10:
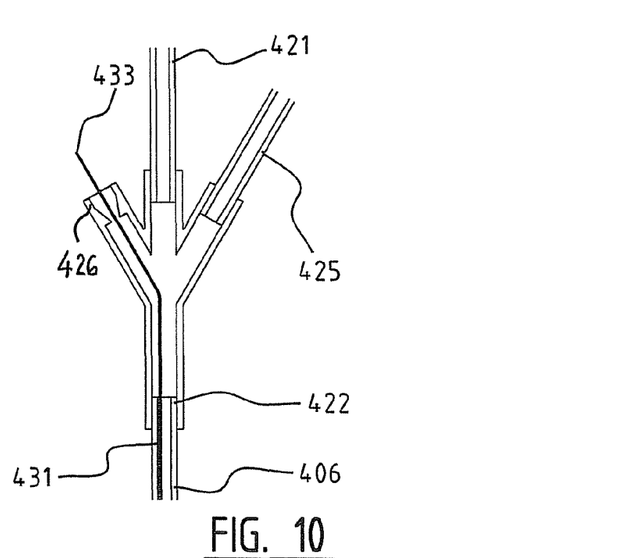
FIG. 10 is a detailed, enlarged scale view of the encircled area X in FIG. 9.

In this embodiment the inflatable member 407 is again filled by means of a syringe which may be connected to a fill connector 420 at the end of a fill line 421. This fill line 421 is again connected to the catheter 406 through a trident connector 423, in this case through the center prong thereof. Also connected to the trident connector 423 is a pilot line 425 carrying a pilot balloon 424. Finally, the proximal end of the wire 431 is guided through the third prong of the trident connector 423. In order to prevent fluid leakage, the proximal end 433 of the pull wire 431 protrudes from this third prong through a valve member, in particular a one-way valve 426 (FIG. 10).

Figure 11:
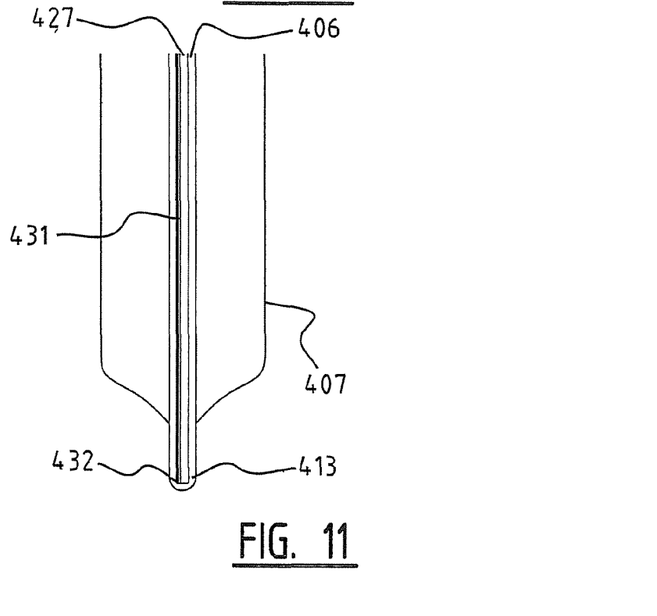
FIG. 11 is a detailed, enlarged scale view of the distal end of the catheter in the fifth embodiment.
Figure 12A:
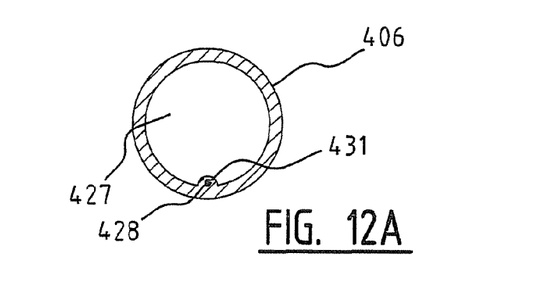
FIGS. 12A and 12B are cross-sectional views of the catheter, showing the various possibilities for accommodating the pull wire.

There are various possibilities for accommodating the pull wire 431 in the catheter 406. The pull wire 431 may be accommodated in the main lumen 427 of the catheter 406 (FIG. 11). This has the advantage of that the use of the guide means 410 entails a minimum of structural modifications. Alternatively, the catheter 406 may have an additional lumen 428 for accommodating the pull wire 431, besides the main lumen 427 for filling the inflatable member 407 with the ultrasonic transmission fluid F (FIG. 12A). In this way interference between the pull wire 431 and the transmission fluid F is again minimized.

Figure 12B:
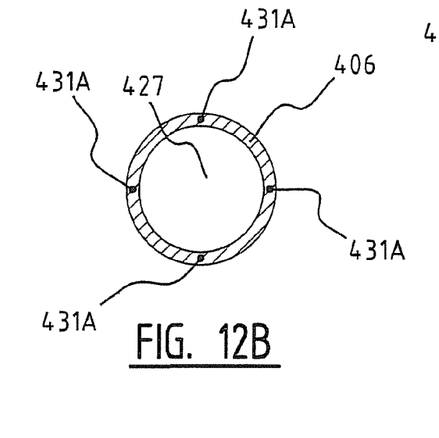

Instead of just a single pull wire, the ultrasonic imaging system may comprise a plurality of pull wires 431A (FIG. 12B), which are spaced in the peripheral direction of the catheter 406. This allows the catheter 406 to be controlled in different directions by manipulating the various pull wires 431. Additionally or alternatively, the distal ends of the various wires 431A may also be spaced in lengthwise direction of the catheter 406 to further improve controllability of the catheter 406.

Thus, the invention provides a method and a system with which an inflatable member that is to be filled with an ultrasound transmission fluid may be swiftly and accurately brought into a predetermined position within the respiratory tract of a patient. This in turn allows certain parts of the circulatory system, in particular the heart or aorta, to be visualized through the respiratory tract, using an imaging device that is arranged in the patient's esophagus, thus providing valuable information during operative surgery.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for ultrasonic imaging of an organ in a patient's body through a part of the patient's respiratory tract, comprising:
   arranging an ultrasonic imaging device in or on the patient's body;
   providing a flexible catheter carrying at least one inflatable member; said flexible catheter having a distal end including a tip;
   fixing a stylet between said at least one inflatable member and said tip of the catheter, such that said stylet has a first end adjacent the tip of the catheter and a second end at a distal end of the inflatable member whereby said stylet does not extend across the entire length of an inner part of the inflatable member;
   introducing said flexible catheter carrying said at least one inflatable member into the respiratory tract;
   positioning said at least one inflatable member at a predetermined location in the respiratory tract;
   wherein said at least one inflatable member is positioned in the respiratory tract by manipulating a proximal end of the flexible catheter;
   filling said at least one inflatable member with an ultrasonic transmission fluid through the flexible catheter; and
   imaging the organ in the patient's body.

2. The method of claim 1, wherein the tip at a distal end of the catheter is shaped to facilitate positioning in the patient's left main bronchus and the stylet is adhesively fixed to the catheter tip.

3. A system for ultrasonic imaging of an organ in a patient's body through a part of the patient's respiratory tract, comprising:
   an ultrasonic imaging device adapted to be arranged in or on the patient's body;
   a flexible catheter carrying at least one inflatable member to be arranged in the respiratory tract; said flexible catheter having a distal end including a tip;
   means for positioning said at least one inflatable member at a predetermined location in the respiratory tract;
   means for filling said at least one inflatable member with an ultrasonic transmission fluid through the flexible catheter;
   wherein the positioning means comprise a stylet fixed between said at least one inflatable member and a distal end of the catheter, said stylet having a first end adjacent the tip of the catheter and a second end at a distal end of the inflatable member such that the stylet does not extend across the entire length of an inner part of the inflatable member; and
   wherein the ultrasonic imaging device is adapted to image the organ in the patient's body.

4. The ultrasonic imaging system of claim 3, wherein the catheter has a main lumen for filling said at least one inflatable member with the ultrasonic transmission fluid, and wherein the stylet is arranged in the main lumen.

5. The ultrasonic imaging system of claim 3, wherein the catheter has a main lumen for filling the inflatable member with the ultrasonic transmission fluid and an additional lumen for accommodating the stylet.

6. The ultrasonic imaging system of claim 3, wherein the catheter has a main lumen for filling said at least one inflatable member with the ultrasonic transmission fluid and wherein the stylet is fixedly arranged in a peripheral wall surrounding the main lumen.

7. The ultrasonic imaging system of claim 3, wherein the stylet is substantially straight.

8. The ultrasonic imaging system of claim 3, wherein the tip that is shaped to facilitate positioning in the patient's left main bronchus and the stylet is adhesively fixed to the catheter tip.

* * * * *